United States Patent [19]
Rozier

[11] Patent Number: 5,326,761
[45] Date of Patent: Jul. 5, 1994

[54] FLUID OPHTHALMIC COMPOSITION BASED ON LIPID MICROPARTICLES CONTAINING AT LEAST ONE ACTIVE PRINCIPLE

[75] Inventor: Annouk Rozier, Clermont-Ferrand, France

[73] Assignee: Merck Sharp & Dohme-Chibret, Paris, France

[21] Appl. No.: 639,478

[22] Filed: Jan. 10, 1991

[30] Foreign Application Priority Data

Jan. 12, 1990 [FR] France ................. 90 00340

[51] Int. Cl.$^5$ ................. A61K 31/535; A61K 31/715
[52] U.S. Cl. ................. 514/235.8; 514/54; 514/912
[58] Field of Search .............. 514/54, 235.8, 912

[56] References Cited

FOREIGN PATENT DOCUMENTS 0227494 7/1987 European Pat. Off. .

OTHER PUBLICATIONS

Remington's Pharmaceutical Sciences, Fifteenth Edition 1975, pp. 716 and 1249–1252.

Primary Examiner—Zohreh Fay
Attorney, Agent, or Firm—Sylvia A. Ayler; Mark R. Daniel; Joseph F. DiPrima

[57] ABSTRACT

There is described a fluid ophthalmic composition which comprises a suspension in a fluid dispersant medium of lipid microparticles containing at least one active principle. The composition enables improved availability of the active principle to be obtained as a result of high intraocular levels.

13 Claims, No Drawings

FLUID OPHTHALMIC COMPOSITION BASED ON LIPID MICROPARTICLES CONTAINING AT LEAST ONE ACTIVE PRINCIPLE

The present invention relates to a fluid ophthalmic composition.

Many ophthalmic compositions are currently available in liquid or solid form, but none of them is, in fact, completely satisfactory.

In effect, liquid ophthalmic compositions, although easy to use, have some drawbacks; in particular, it is difficult to obtain a sustained or delayed action of the active principle which they contain.

Similarly solid or semi-solid ophthalmic compositions which, for their part, permit a longer-lasting action of the active principle, are not liked by the users on account of their method of application. In effect, they are presented in the form of a solid insert or an ointment to be introduced into the conjunctival cul-de-sac.

The present invention relates to a fluid ophthalmic composition which is easy to use, enabling the availability of the active principle to be improved, especially as a result of high intraocular levels.

The present invention proposes a fluid ophthalmic composition, characterized in that it comprises a suspension, in a fluid dispersant medium, of lipid microparticles containing at least one pharmaceutically active principle.

In the fluid ophthalmic compositions according to the present invention, the lipid microparticles preferably consist of a lipid phase capable of melting at the temperature of the conjunctival cul-de-sac between 30° and 40° C., in order to release the active principle.

Nevertheless, it is possible to contrive microparticles which do not actually melt but which can be removed by simple disintegration, as well as pasty particles which can line the conjunctival cul-de-sac.

By way of example, the microparticles may be prepared from a lipid base or from a mixture of fatty acids melting at 32°–38° C. The bases usable for the preparation of suppositories are, for example, very suitable.

Thus, preliminary trials were performed with semi-synthetic glycerides, in particular the base Suppocire (marketed by the company Gatefosse).

The fluid dispersant medium preferably consists of an aqueous solution of hydrophilic polymer, for example of polyvinyl alcohols, hydroxylated celluloses, polyvinylpyrrolidone or poloxamers, as well as of derivatives of these compounds or alternatively of polysaccharides or natural or synthetic polysaccharide derivatives, for example phase-transition polymers.

It has, in effect, been demonstrated that polysaccharide solutions obtained by fermentation of a microorganism, which are aqueous polysaccharide solutions of a type undergoing phase transition through the effect of an increase in ionic strength, are especially suitable according to the invention.

Thus, according to the invention, an extracellular anionic heteropolysaccharide produced by the bacterium Pseudomonas elodea, known under the name gellan gum, is preferably used. The compound known by the brand name Gelrite, which is a grade of clarified and only slightly acetylated gellan gum (marketed by the company Kelco), is preferably used.

By choosing the surface tensions of the components of the composition, it will be sought to obtain products which can be dispensed dropwise, in particular with the usual droppers.

Moreover, these fluid ophthalmic compositions can be modified so as to postpone the release of the active principle by increasing, for example, the melting point of the lipid phase.

It is also possible to produce a stepwise-release ophthalmic composition with an active principle present in the fluid dispersant medium, which principle will be immediately available, and an identical or different active principle in the lipid phase, which will be available only after a latent period or for a longer period.

The value of this ophthalmic composition hence lies in the fact of combining some of the properties of ophthalmic ointments and the possibility of solubilizing water-insoluble active principles with the ease of administration of liquid formulae.

In the compositions according to the invention, it is possible to use a wide diversity of active principles. The latter may be chosen, in particular, from the following pharmaceutical compounds:

antibacterial substances such as beta-lactam antibiotics, for example cefoxitin, n-formamidoylthienamycin and other thienamycin derivatives, tetracyclines, chloramphenicol, neomycin, carbenicillin, colistin, penicillin G, polymyxin B, vancomycin, cefazolin, cefaloridine, chibrorifamycin, gramicidin, bacitracin and sulphonamides; aminoglycoside antibiotics such as gentamicin, kanamycin, amikacin, sisomicin and tobramycin; nalidixic acid and its analogues such as norfloxacin and the antimicrobial combination of fluoroalanine/pentizidone, nitrofurazones and their analogues;

antihistaminics and decongestants such as pyrilamine, chlorpheniramine, tetrahydrazoline, antazoline and their analogues;

anti-inflammatories such as cortisone hydrocortisone, hydrocortisone acetate, betamethasone, dexamethasone, dexamethasone sodium phosphate, prednisone, methylprednisolone sodium phosphate, triamcinolone, indomethacin, sulindac, its salts and corresponding sulphides, and their analogues;

miotics and anticholinergics such as echothiopate, pilocarpine, physostigmine salicylate, diisopropyl fluorophosphate, epinephrine, dipivalylepinephrine, neostigmine, echothiopate iodide, demecarium bromide, carbamoylcholine chloride, methacholine, bethanechol and their analogues;

mydriatics such as stropine, homatropine, scopolamine, hydroxyamphetamine, ephedrine, cocaine, tropicamide, phenylephrine, cyclopentolate, oxyphenonium, eucatropine and their analogues.

Other drugs used in the treatment of eye conditions and lesions, such as:

antiglaucoma drugs, for example timolol and R-timolol and a combination of timolol or R-timolol with pilocarpine, and also many other adrenergic agonists and/or antagonists; epinephrines and a complex of epinephrine or prodrugs, and dipivefrin derivatives and hyperosmotic agents such as glycerol, mannitol and urea;

antiparasitic compounds and/or antiprotozoal compounds such as ivermectin; pyrimethamine, trisulphapyrimidine, clindamycin and corticosteroid preparations;

compounds having antiviral activity such as acyclovir, 5-iodo-2'-deoxyuridine (IDU), adenosine arabinoside (Ara-A), trifluorothymidine, and interferon and interferon-inducing agents such as polyI.polyC, carbonic anhydrase inhibitors such as acetazolamide, dichlorphenamide, 2-(P-hydroxyphenyl)thio-5-thiophenesulphonamide, 6-hydroxy-2-benzothiazolesulphonamide, 6-pivaloyloxy-2-benzothiazolesulphonamide, MK 927 and MK 417;

antifungal agents such as amphotericin B, nystatin, flucytosine, natamycin and miconazole;

anaesthetic agents such as etidocaine, cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

Ophthalmic diagnostic agents such as:

a) those which are used for examining the retina, such as fluorescein sodium;

b) those which are used for examining the conjunctiva, cornea and lachrymal apparatus, such as fluroescein and rose bengal; and c) those which are used for examining abnormal responses of the pupil, such as methacholine, cocaine, adrenaline, atropine, hydroxyamphetamine and pilocarpine;

Ophthalmic agents used as surgical aids, such as alphachymotrypsin and hyaluronidase;

Chelating agents such as ethylenediaminetetraacetic acid (ETDA) and deferoxamine;

Immunosuppressants and antimetabolites such as methotrexate, cyclophosphamide, 6-mercaptopurine and azathioprine; and antibiotic/anti-inflammatory combinations such as the combination neomycin sulphate/dexamethasone sodium phosphate, and combinations concomitantly treating glaucoma, for example a timolol maleate/aceclidine combination.

The ophthahic composition according to the invention must naturally fulfil the criteria for use in this field, in particular it should preferably be isotonic and have a pH lying between 5.0 and 8.0. Thus, it may incorporate other components such as tonicity regulators, preservatives and buffer systems.

The present invention also relates to a process for preparing this ophthahic composition, characterized in that:

the active principle is dissolved in the lipid base at the melting point of the latter;

the fluid dispersant medium and, optionally, the other components are dissolved in water at a temperature close to the above melting point, the aqueous mixture obtained is added with vigorous stirring to the lipid phase, this new mixture is cooled abruptly so as to cause solidification of the lipid droplets to microparticles.

The example below will enable other features and advantages of the present invention to be demonstrated.

EXAMPLE 1

A fluid ophthahic composition of the following formulation is produced according to the process described above:

| | |
|---|---|
| Timolol base | 0.25 g |
| Suppocie AP | 4.00 g |
| Mannitol | 4.50 g |
| Tromethamine | 0.091 g |
| Hydrochloric acid, N | qs pH 8.0–85 |
| Gelrite (L-679, 139000K) | 0.60 g |
| Benzalkonium chloride | 0.01 g |

Mannitol is used as a tonicity regulator, benzalkonium chloride is used as a preservative and the combination tromethamine/hydrochloric acid constitutes the buffer system which is effective at the pH in question.

The timolol is dissolved in Suppocire melted beforehand at 40° C. The mannitol, tromethamine, N hydrochloric acid and Gelrite are, for their part, dissolved in water, heated to 40° C. and added with vigorous stirring to the lipid phase. The mixture thereby obtained is then cooled abruptly in order to obtain solidification of the lipid droplets.

A variant of this process may be carried out by performing, in the first place, in the presence of surfactants, emulsification in an aqueous phase of the organic phase comprising the organic solvent, the active principle and the lipid excipient.

Evaporation of the organic solvent is then carried out under vacuum.

The ophthalmic composition thus prepared was compared with a reference ophthalmic composition simply comprising timolol in Gelrite. The results obtained are presented in Tables 1, 2 and 3 below. The intraocular levels obtained after instillation of the ophthalmic composition according to the invention demonstrated a greater activity of the latter.

TABLE 1

| CONCENTRATIONS IN THE AQUEOUS HUMOUR AFTER INSTILLATION OF PREPARATIONS CONTAINING 0.25% OF TIMOLOL IN ALBINO RABBITS | | | | | |
|---|---|---|---|---|---|
| Time subsequent | μg of TIMOLOL/ml | | | | |
| to administration | 10 min | 0.5 h | 1 h | 2 h | 4 h |
| Composition according to the invention (microparticles in GELRITE) | 4.15 ± 1.56 | 7.46 ± 2.96 | 4.43 ± 0.88 | 1.95 ± 0.50 | 0.24 ± 0.08 |
| Control composition (GELRITE) | 0.98 ± 0.34 | 3.17 ± 1.29 | 3.67 ± 1.26 | 1.72 ± 0.91 | 0.24 ± 0.04 |

These results correspond to the mean for 12 eyes ± standard deviation.

TABLE 2

| CONCENTRATIONS IN THE CORNEA AFTER INSTILLATION OF PREPARATIONS CONTAINING 0.25% OF TIMOLOL IN ALBINO RABBITS | | | | | |
|---|---|---|---|---|---|
| Time subsequent | μg of TIMOLOL/ml | | | | |
| to administration | 10 min | 0.5 h | 1 h | 2 h | 4 h |
| Composition according to the invention (microparticles in GELRITE) | 89.86 ± 26.44 | 60.56 ± 18.35 | 36.51 ± 8.17 | 19.73 ± 5.02 | 5.68 ± 2.09 |

TABLE 2-continued

CONCENTRATIONS IN THE CORNEA AFTER INSTILLATION OF PREPARATIONS CONTAINING 0.25% OF TIMOLOL IN ALBINO RABBITS

| Time subsequent to administration | μg of TIMOLOL/ml | | | | |
|---|---|---|---|---|---|
|  | 10 min | 0.5 h | 1 h | 2 h | 4 h |
| Control composition (GELRITE) | 44.1 ± 8.6 | 46.1 ± 17.1 | 35.7 ± 11.0 | 16.3 ± 10.3 | 3.3 ± 1.0 |

These results correspond to the mean for 12 eyes ± standard deviation.

TABLE 3

CONCENTRATIONS IN THE IRIS + CILIARY BODY AFTER INSTILLATION OF PREPARATIONS CONTAINING 0.25% OF TIMOLOL IN ALBINO RABBITS

| Time subsequent to administration | μg of TIMOLOL/ml | | | | |
|---|---|---|---|---|---|
|  | 10 min | 0.5 h | 1 h | 2 h | 4 h |
| Composition according to the invention (microparticles in GELRITE) | 6.90 + 1.89 | 8.95 + 2.59 | 4.57 + 0.95 | 4.08 + 1.67 | 1.27 + 1.00 |
| Control composition (GELRITE) | 5.16 ± 2.93 | 6.21 ± 3.05 | 5.22 ± 2.12 | 2.48 ± 0.94 | 1.64 ± 0.96 |

These results correspond to the mean for 12 eyes ± standard deviation.

I claim:

1. In a fluid ophthalmic composition comprising a fluid dispersant medium and an effective amount of at least one opthalmic pharmaceutical or diagnostic active principle, the improvement wherein the active principle is contained in lipid microparticles suspended in the fluid dispersant medium, wherein the lipid microparticles are prepared from a lipid base having a melting point of between 30° and 40° C.

2. A fluid ophthalmic composition according to one of claim 1, characterized in that the microparticles are prepared from a mixture of fatty acids having a melting point of between 32° and 38° C.

3. A fluid ophthalmic composition according to one of claims 1 and 2, characterized in that the fluid dispersant medium is chosen from hydrophilic polymers and phase-transition polymers.

4. A fluid ophthalmic composition according to one of claims 1 to 3, characterized in that the fluid dispersant medium is chosen from hydroxylated celluloses and their derivatives and polyvinyl alcohols.

5. A fluid ophthalmic composition according to one of claims 1 to 4, characterized in the fluid dispersant medium is a gellan gum.

6. A fluid ophthalmic composition according to one of claims 1 to 5, characterized in that the fluid dispersant medium also contains an ophthalmic pharmaceutical or diagnostic active principle.

7. A fluid opthalmic composition according to claim 6, characterized in that the opthalmic pharmaceutical or diagnostic active principle is identical in the fluid dispersant medium and the lipid microparticles.

8. Ophthalmic composition according to one of claims 1 to 7, characterized in that the active principle is chosen from antiglaucoma agents, antibiotics and antiviral agents.

9. A fluid ophthalmic composition according to one of claims 1 to 8, characterized in that the active principle is timolol.

10. A fluid ophthalmic composition according to one of claims 1 to 9, characterized in that it contains other components chosen from tonicity regulators, preservatives and buffer systems.

11. Process for preparing the fluid ophthalmic composition according to claim 1, characterized in that:
the active principle is dissolved in the lipid base at the melting point of the latter;
the fluid dispersant medium and, optionally, the other components are dissolved in water at a temperature close to the above melting point,
the aqueous mixture obtained is added with vigorous stirring to the lipid phase,
this new mixture is cooled abruptly so as to cause solidification of the lipid droplets to microparticles.

12. Process for preparing the fluid ophthalmic composition according to claim 1, characterized in that the components of the composition are emulsified in an aqueous phase, optionally in the presence of surfactants and an organic solvent, the said organic solvent being evaporated off when the emulsification is complete.

13. Fluid ophthalmic composition according to one of claims 1 to 10, characterized in that it is presented in the form of a liquid capable of being applied in droplet form.

* * * * *